(12) United States Patent
Nemiraj et al.

(10) Patent No.: US 12,324,749 B2
(45) Date of Patent: Jun. 10, 2025

(54) IMPACTION HANDLE FOR IMPLANTING A TIBIAL TRAY OF AN ORTHOPAEDIC KNEE PROSTHESIS AND ASSOCIATED METHOD OF MAKING THE SAME

(71) Applicant: DEPUY SYNTHES PRODUCTS, INC., Raynham, MA (US)

(72) Inventors: Rakshak Nemiraj, Karnataka (IN); Nicholas A. Miltner, Fort Wayne, IN (US); Colton D. Steiner, Warsaw, IN (US); Bernice A. Gatrell, Columbia City, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 340 days.

(21) Appl. No.: 17/872,350

(22) Filed: Jul. 25, 2022

(65) Prior Publication Data
US 2024/0024128 A1    Jan. 25, 2024

(51) Int. Cl.
*A61F 2/46* (2006.01)
*B33Y 80/00* (2015.01)

(52) U.S. Cl.
CPC ............. *A61F 2/461* (2013.01); *B33Y 80/00* (2014.12); *A61F 2002/4627* (2013.01); *A61F 2002/4681* (2013.01)

(58) Field of Classification Search
CPC .......................... A61F 2002/4681; A61F 2/461
See application file for complete search history.

(56) References Cited

U.S. PATENT DOCUMENTS

| | | | | |
|---|---|---|---|---|
| 319,095 A | * | 6/1885 | Joel | G04D 3/045 |
| | | | | 279/2.12 |
| 4,364,389 A | * | 12/1982 | Keller | A61F 2/461 |
| | | | | 606/86 R |
| 5,059,196 A | * | 10/1991 | Coates | A61F 2/461 |
| | | | | 269/48.3 |
| 5,061,270 A | | 10/1991 | Aboczky | |
| 5,062,852 A | | 11/1991 | Dorr et al. | |
| D337,639 S | | 7/1993 | Beckman | |

(Continued)

FOREIGN PATENT DOCUMENTS

DE    10013331 A1    9/2001
EP      780090 A1    6/1997

(Continued)

OTHER PUBLICATIONS

Sigma Fixed Reference Surgical Technique, DePuy Orthopaedics, Inc. 2010, 52 pages.

(Continued)

*Primary Examiner* — David W Bates
(74) *Attorney, Agent, or Firm* — Barnes & Thornburg LLP

(57) ABSTRACT

An impaction handle for use during a surgical procedure to implant a tibial tray into a surgically-prepared proximal end of a tibia includes an impact plate defining a proximal end of the impaction handle and an impact head defining a distal end of the impaction handle. The impaction handle also has an elongated shaft extending between the impact plate and the impact head, along with a locking mechanism to lock the handle to the tibial tray. The impact plate, the impact head, the elongated shaft, and the locking mechanism of the impaction handle collectively define a single monolithic metallic component.

11 Claims, 7 Drawing Sheets

(56) References Cited

U.S. PATENT DOCUMENTS

| | | | |
|---|---|---|---|
| 5,484,132 A * | 1/1996 | George | A63B 29/024 |
| | | | 248/231.9 |
| 5,571,111 A * | 11/1996 | Aboczky | A61F 2/4609 |
| | | | 606/91 |
| 5,683,399 A * | 11/1997 | Jones | A61F 2/4609 |
| | | | 606/91 |
| 5,732,992 A * | 3/1998 | Mauldin | A61F 2/461 |
| | | | 606/205 |
| 5,788,701 A * | 8/1998 | McCue | A61B 17/1604 |
| | | | 606/88 |
| 5,902,339 A | 5/1999 | Keller | |
| 6,520,966 B1 | 2/2003 | Kohler et al. | |
| 6,663,636 B1 | 12/2003 | Lin | |
| 7,048,742 B2 * | 5/2006 | Keller | A61F 2/461 |
| | | | 606/88 |
| 8,128,703 B2 | 3/2012 | Hazebrouck et al. | |
| 8,277,460 B2 * | 10/2012 | McMillan | A61B 17/92 |
| | | | 606/99 |
| 8,303,601 B2 * | 11/2012 | Bandeira | A61B 17/025 |
| | | | 606/90 |
| 8,317,870 B2 | 11/2012 | Wagner et al. | |
| 8,435,241 B2 * | 5/2013 | Correia | A61B 17/92 |
| | | | 606/86 R |
| 8,597,302 B2 | 12/2013 | Beedall et al. | |
| 8,870,886 B2 * | 10/2014 | Burgi | A61F 2/4609 |
| | | | 606/91 |
| 8,986,390 B2 * | 3/2015 | Wogoman | A61F 2/4684 |
| | | | 623/20.29 |
| 9,039,710 B2 | 5/2015 | Blaylock et al. | |
| 9,439,780 B2 * | 9/2016 | Witt | A61F 2/4609 |
| 9,820,857 B2 | 11/2017 | Wyss et al. | |
| 10,092,421 B2 | 10/2018 | Edwards et al. | |
| 10,238,439 B2 * | 3/2019 | Prybis | A61B 17/80 |
| 2003/0109929 A1 | 6/2003 | Keller | |
| 2005/0124998 A1 * | 6/2005 | Coon | A61F 2/461 |
| | | | 606/99 |
| 2006/0116769 A1 | 6/2006 | Marnay et al. | |
| 2006/0136067 A1 * | 6/2006 | Pendleton | A61F 2/461 |
| | | | 606/86 R |
| 2006/0200162 A1 | 9/2006 | Farling et al. | |
| 2007/0167952 A1 * | 7/2007 | Burgi | A61B 17/1666 |
| | | | 606/99 |
| 2008/0119941 A1 | 5/2008 | Seo et al. | |
| 2009/0036909 A1 * | 2/2009 | Perry | A61F 2/461 |
| | | | 606/157 |
| 2011/0301613 A1 | 12/2011 | Green, II | |
| 2012/0123429 A1 | 5/2012 | Beedall et al. | |
| 2012/0143204 A1 * | 6/2012 | Blaylock | A61F 2/461 |
| | | | 623/20.35 |
| 2013/0006371 A1 | 1/2013 | Wogoman et al. | |
| 2013/0018382 A1 * | 1/2013 | Jones | A61F 2/4603 |
| | | | 623/20.35 |
| 2013/0144296 A1 * | 6/2013 | Yoko | A61B 17/1764 |
| | | | 606/84 |
| 2013/0184829 A1 | 7/2013 | Wyss et al. | |
| 2014/0094812 A1 * | 4/2014 | Edwards | A61F 2/461 |
| | | | 606/88 |
| 2014/0094821 A1 * | 4/2014 | Wagner | A61F 2/461 |
| | | | 606/99 |
| 2014/0276838 A1 * | 9/2014 | Tsukayama | G05G 1/04 |
| | | | 74/491 |
| 2014/0277479 A1 * | 9/2014 | Raymond | A61F 2/4611 |
| | | | 623/17.16 |
| 2014/0277541 A1 * | 9/2014 | Wyss | A61F 2/461 |
| | | | 623/20.32 |
| 2015/0366677 A1 * | 12/2015 | Porzel | A61L 27/50 |
| | | | 623/20.35 |
| 2016/0270929 A1 * | 9/2016 | Sweitzer | A61F 2/461 |
| 2018/0214281 A1 * | 8/2018 | Dykema | A61F 2/461 |
| 2020/0205815 A1 * | 7/2020 | Nalagatla | B33Y 40/20 |
| 2020/0253749 A1 * | 8/2020 | Anthony | A61B 17/15 |

FOREIGN PATENT DOCUMENTS

| | | |
|---|---|---|
| WO | 9325164 A1 | 12/1993 |
| WO | 2011004140 A2 | 1/2011 |
| WO | 2011004140 A3 | 4/2011 |

OTHER PUBLICATIONS

Attune Knee System Revision Solutions, Attune Revision Knee System Fixed Bearing Surgical Technique, DePuy Synthes, 2017, 219 pages.

Attune Knee System INTUITION Instruments Surgical Technique, DePuy Synthes, 2022, 136 pages.

* cited by examiner

IMPACTION HANDLE FOR IMPLANTING A TIBIAL TRAY OF AN ORTHOPAEDIC KNEE PROSTHESIS AND ASSOCIATED METHOD OF MAKING THE SAME

TECHNICAL FIELD

The present disclosure relates generally to orthopaedic surgical instruments and, more particularly, to surgical instruments used to install a tibial tray of an orthopaedic knee prosthesis.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component.

To facilitate the replacement of the natural joint with a prosthesis, orthopaedic surgeons use a variety of orthopaedic surgical instruments such as, for example, impaction handles, cutting blocks, drill guides, and other surgical instruments.

SUMMARY

According to one aspect, an orthopaedic surgical instrument for use during a surgical procedure to implant a tibial tray into a surgically-prepared proximal end of a tibia includes an impaction handle having an impact plate defining a proximal end of the impaction handle and an impact head defining a distal end of the impaction handle. The impact head has an impact surface that is sized and shaped to be positioned on a superior surface of the tibial tray when the impaction handle is used to impact the tibial tray. The impaction handle also has an elongated shaft extending between the impact plate and the impact head. The elongated shaft is hollow along its entire length. A locking mechanism of the impaction handle is positioned in the impact head. The locking mechanism includes a locking tab that is movable between a locked positioned in which the locking tab is extended outwardly from the impact head so as to be received into a locking slot defined in the tibial tray, and an unlocked position in which the locking tab is retracted inwardly toward the impact head so as to remove the locking tab from the locking slot of the tibial tray. The impact plate, the impact head, the elongated shaft, and the locking mechanism of the impaction handle collectively define a single monolithic metallic component.

In an embodiment, the single monolithic metallic component defined by the impact plate, the impact head, the elongated shaft, and the locking mechanism of the impaction handle includes a plurality of laminations.

In an embodiment, the locking tab is defined in an end of a flange, with the flange being slidable relative to the impact head so as to move the locking tab between its locked position and its unlocked position. In such an embodiment, the locking mechanism may further include an eccentric cylinder having a tip. The tip of the eccentric cylinder is positioned in a slot defined in the flange such that rotation of the of the eccentric cylinder causes the flange to slide relative to the impact head.

In an embodiment, the single monolithic metallic component defined by the impact plate, the impact head, the elongated shaft, and the locking mechanism of the impaction handle includes a plurality of laminations, with at least one of the plurality of laminations defining a portion of each of the impact head, the flange of the locking mechanism, and the eccentric cylinder of the locking mechanism.

In such an embodiment, at least one of the plurality of laminations may define a portion of each of the impact head, the flange of the locking mechanism, and the tip of the eccentric cylinder of the locking mechanism.

In an embodiment, the eccentric cylinder rotates about an axis of rotation, with the tip of the eccentric cylinder having a longitudinal axis that is offset from the axis of rotation of the eccentric cylinder.

The eccentric cylinder may have a lever extending outwardly therefrom such that movement of the lever causes rotation of the eccentric cylinder.

According to another aspect, an orthopaedic surgical instrument for use during a surgical procedure to implant a tibial tray into a surgically-prepared proximal end of a tibia includes a single monolithic metallic impaction handle having a plurality of laminations of metallic material. The impaction handle includes an impact plate defining a proximal end of the impaction handle, and an impact head defining a distal end of the impaction handle. The impact head has an impact surface that is sized and shaped to be positioned on a superior surface of the tibial tray when the impaction handle is used to impact the tibial tray. An elongated shaft extends between the impact plate and the impact head. The elongated shaft is hollow along its entire length. A locking mechanism is positioned in the impact head. The locking mechanism includes a locking tab that is movable between a locked positioned in which the locking tab is extended outwardly from the impact head so as to be received into a locking slot defined in the tibial tray, and an unlocked position in which the locking tab is retracted inwardly toward the impact head so as to remove the locking tab from the locking slot of the tibial tray.

In an embodiment, the locking tab is defined in an end of a flange, with the flange being slidable relative to the impact head so as to move the locking tab between its locked position and its unlocked position. In such an embodiment, the locking mechanism may further include an eccentric cylinder having a tip. The tip of the eccentric cylinder is positioned in a slot defined in the flange such that rotation of the of the eccentric cylinder causes the flange to slide relative to the impact head.

In an embodiment, at least one of the plurality of laminations defines a portion of each of the impact head, the flange of the locking mechanism, and the eccentric cylinder of the locking mechanism.

In such an embodiment, at least one of the plurality of laminations may define a portion of each of the impact head, the flange of the locking mechanism, and the tip of the eccentric cylinder of the locking mechanism.

In an embodiment, the eccentric cylinder rotates about an axis of rotation, with the tip of the eccentric cylinder having a longitudinal axis that is offset from the axis of rotation of the eccentric cylinder.

The eccentric cylinder may have a lever extending outwardly therefrom such that movement of the lever causes rotation of the eccentric cylinder.

According to another aspect, a method of making an impaction handle for use during a surgical procedure to implant a tibial tray into a surgically-prepared proximal end of a tibia includes layering metallic material in a fabrication machine so as to simultaneously form an impact head and a locking mechanism positioned in the impact head. In such a manner, the locking mechanism includes a locking tab that is movable between a locked positioned in which the locking tab is extended outwardly from the impact head, and an unlocked position in which the locking tab is retracted inwardly into the impact head.

The method may also include layering metallic material in the fabrication machine so as to form an elongated body onto the impact head. The method may also include layering metallic material in the fabrication machine so as to form an impact flange onto the elongated body.

In an embodiment, the method includes forming the impact head and the locking mechanism as a single monolithic component.

In an embodiment, the method includes forming the impact head and the locking mechanism as a single monolithic component having a plurality of laminations of metallic material.

In an embodiment, the method includes operating a three-dimensional metal printer to fabricate the impaction handle by forming laminations of metallic material.

BRIEF DESCRIPTION OF THE DRAWINGS

The detailed description particularly refers to the following figures, in which.

DETAILED DESCRIPTION OF THE DRAWINGS

Figure 1:
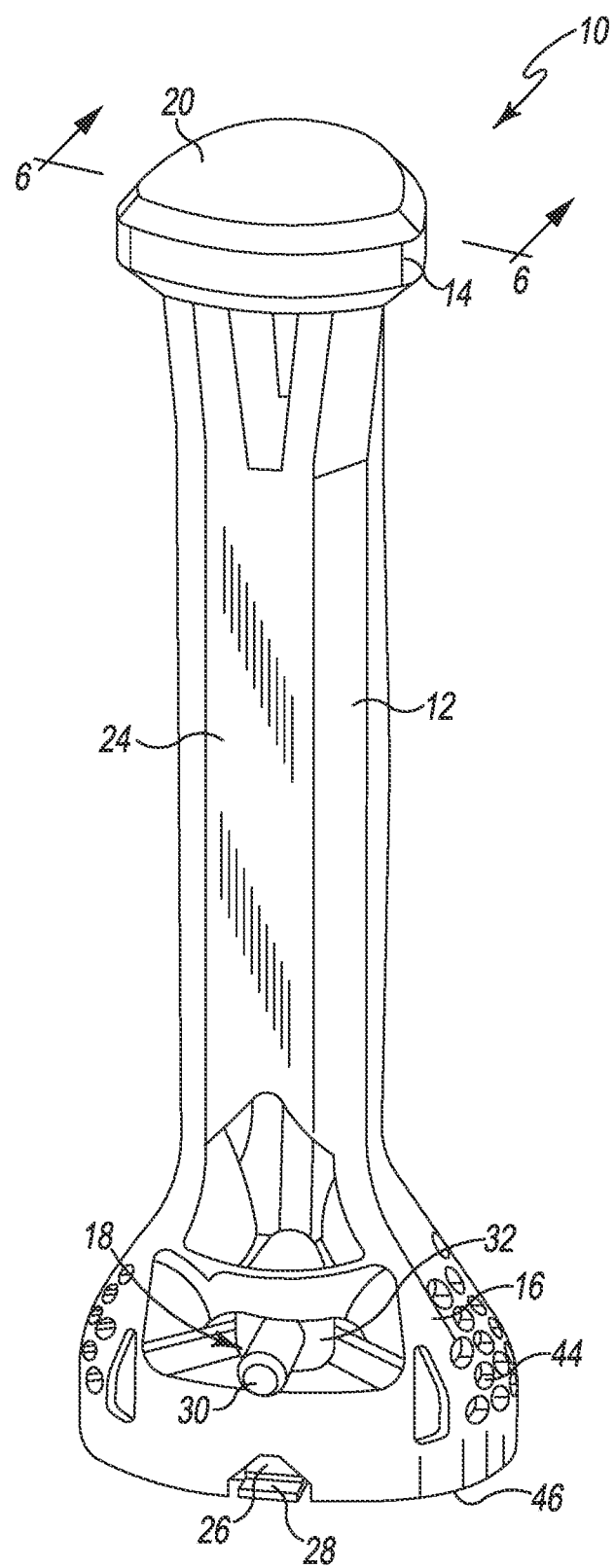
FIG. 1 is a perspective view of an impaction handle for use in implanting a tibial tray of an orthopaedic knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-6, there is shown an orthopaedic surgical instrument—illustratively embodied as an impaction handle 10—for implanting a tibial tray of a knee prosthesis into a surgically-prepared proximal end of a patient's tibia during an orthopaedic surgical procedure. The impaction handle 10 includes an elongated shaft 12 having an impact plate 14 on its proximal end and an impact head 16 on its distal end. A locking mechanism 18 is positioned in the impact head 14. The locking mechanism is operable to lock the impaction handle 10 to a tibial tray 50 (see FIG. 7) of a knee prosthesis during implantation of the tray.

In the illustrative embodiment, the impaction handle 10 is a single monolithic component formed from a metallic material such as, for example, stainless steel. In such a way, the elongated shaft 12, the impact plate 14, the impact head 16, and the locking mechanism 18 form a single monolithic metallic component. As described in more detail below, the impaction handle 10 is formed by Direct Metal Laser Sintering (DMLS), also known as Selective Laser Sintering (SLS), which is a form of 3-D printing technology. In DMLS, the impaction handle 10 is formed in a layer-by-layer fashion using laser sintering in which light fuses metallic powder, forming the metallic structures that define the impaction handle 10. It should be appreciated that other forms of 3-D printing technology such as, for example, optical fabrication, photo-solidification, or resin printing may be used to fabricate the impaction handle 10.

In the exemplary embodiment described herein, the impact plate 14 of the impaction handle 10 includes a rounded metal strike surface 20 formed in the proximal end of the impact plate 14. In use, the surgeon holds the impaction handle 10 via a grip 24 and strikes the strike surface 20 with a surgical mallet, sledge, or other impaction tool to drive the tibial tray 50 into the surgically-prepared proximal end of the patient's tibia. The impact plate 14 may also be embodied with one or more flanges extending radially outwardly therefrom (not shown). Such flanges serve to protect the surgeon's hand on the grip 24 during impaction. Moreover, such flanges can be impacted from their underside surface if the impaction handle 10 is used to extract a tibial tray 50.

The locking mechanism 18 of the impaction handle 10 is configured to lock the impaction handle 10 to the tibial tray 50 during installation of the same in the patient's surgically-prepared proximal tibia. Although other mechanisms may be used, in the exemplary embodiment described herein, the locking mechanism 18 includes a cam-driven slideable flange 26 having a locking tab 28 on its distal end. The locking tab 28 of the locking mechanism 16 is movable between a locked positioned in which the locking tab 28 is extended outwardly from the impact head 16 so as to be received into a locking slot 52 defined in the tibial tray 50 (see FIG. 7), and an unlocked position in which the locking tab 28 is retracted inwardly toward the impact head 16 so as to be removed from the locking slot 52 of the tibial tray 50 thereby allowing the locking handle 10 to be separated from the tibial tray 50.

Figure 3:
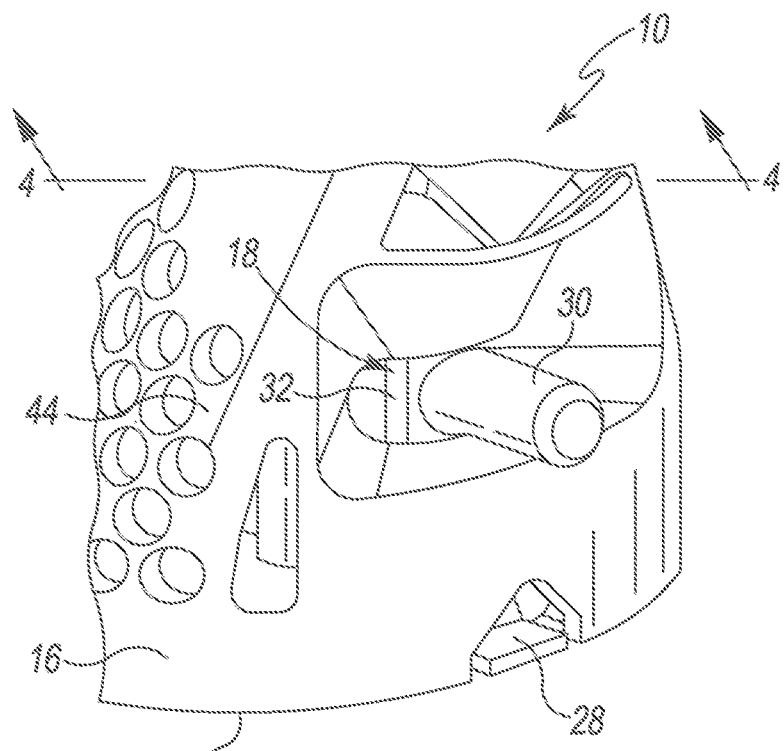
FIG. 3 is an enlarged fragmentary view of the impaction handle of FIG. 1 showing the handle's impact head and locking mechanism in greater detail.
Figure 4:
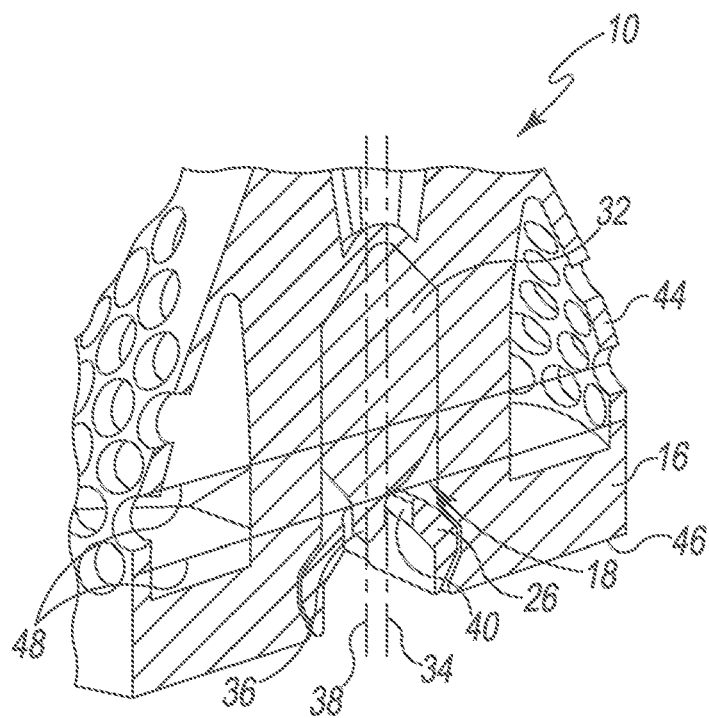
FIG. 4 is a fragmentary cross sectional view of the impaction handle taken along the line 4-4 of FIG. 3, as viewed in the direction of the arrows.
Figure 5:
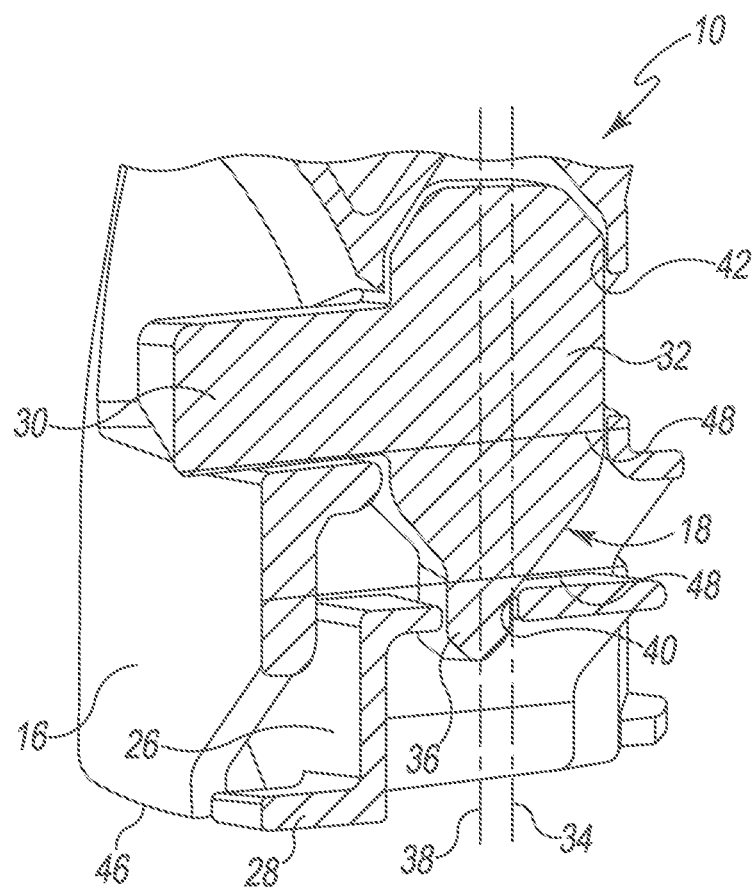
FIG. 5 is a fragmentary cross sectional view of the impaction handle taken along the line 5-5 of FIG. 2, as viewed in the direction of the arrows.

The locking mechanism 18 includes a user-operated lever 30 to allow for movement of the locking tab 28 between its locked position and unlocked position. As can be seen in FIGS. 3-5, the locking mechanism 18 includes an eccentric cylinder 32. The lever 30 is integrally formed with, and extends outwardly from, the round outer surface of the eccentric cylinder 32. As can be seen in FIGS. 4 and 5, the eccentric cylinder 32 rotates about an axis of rotation 34. The eccentric cylinder 32 has a tip 36 formed in its distal end. The tip 36 has a longitudinal axis 38 that is offset from the cylinder's rotational axis 34. As can be seen in FIGS. 4 and 5, the tip 36 of the eccentric cylinder 32 is received into a slot 40 formed in the slideable flange 26. Due to the offset nature of the tip 36 relative to the cylinder's axis of rotation 34, rotation of the lever 30 (and hence the eccentric cylinder 32) in a rightward direction (as viewed in the perspective of FIG. 3) causes the cylinder's tip 36 to engage the sidewalls of the flange's slot 40 so as to urge the slideable flange 26 in a forward direction (as viewed in the perspective of FIG. 3) thereby extending the locking tab 28 outwardly from the impact head 16 thus allowing the locking tab 28 to be positioned in its locked position. Oppositely, rotation of the lever 30 (and hence the eccentric cylinder 32) in a leftward direction (as viewed in the perspective of FIG. 3) causes the cylinder's tip 36 to engage the sidewalls of the flange's slot 40 so as to urge the slideable flange 26 in a backward direction (as viewed in the perspective of FIG. 3) thereby retracting the locking tab 28 inwardly toward the impact head 16 thus allowing the locking tab 28 to be positioned in its unlocked position.

Figure 2:
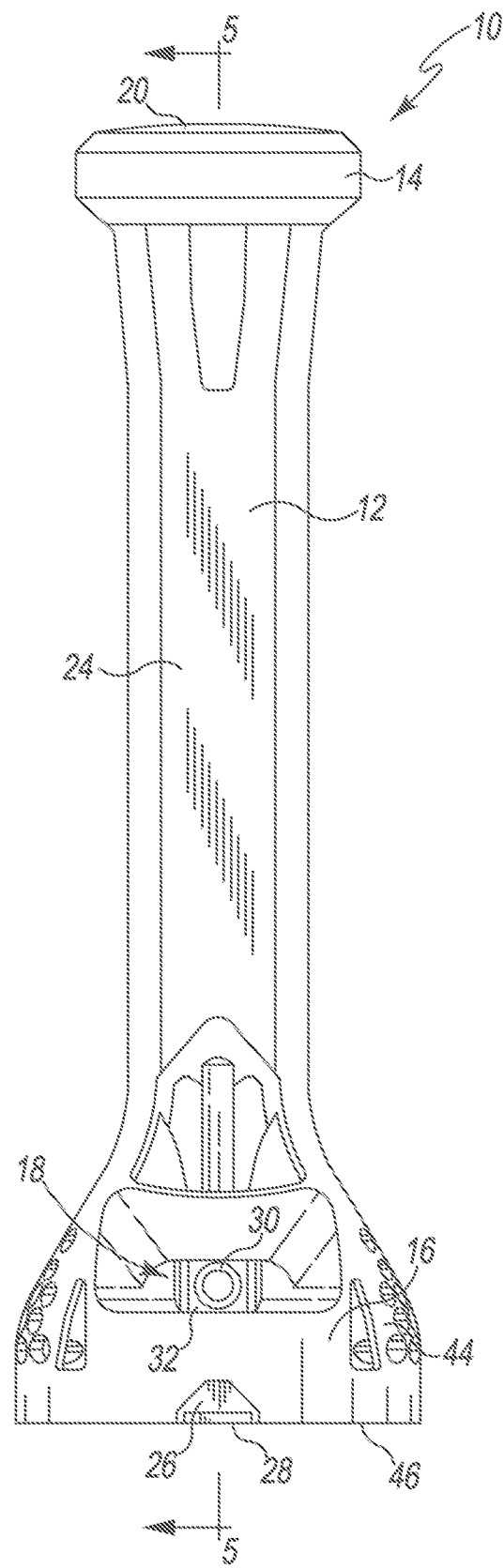
FIG. 2 is a front elevational view of the impaction handle of FIG. 1.
Figure 6:
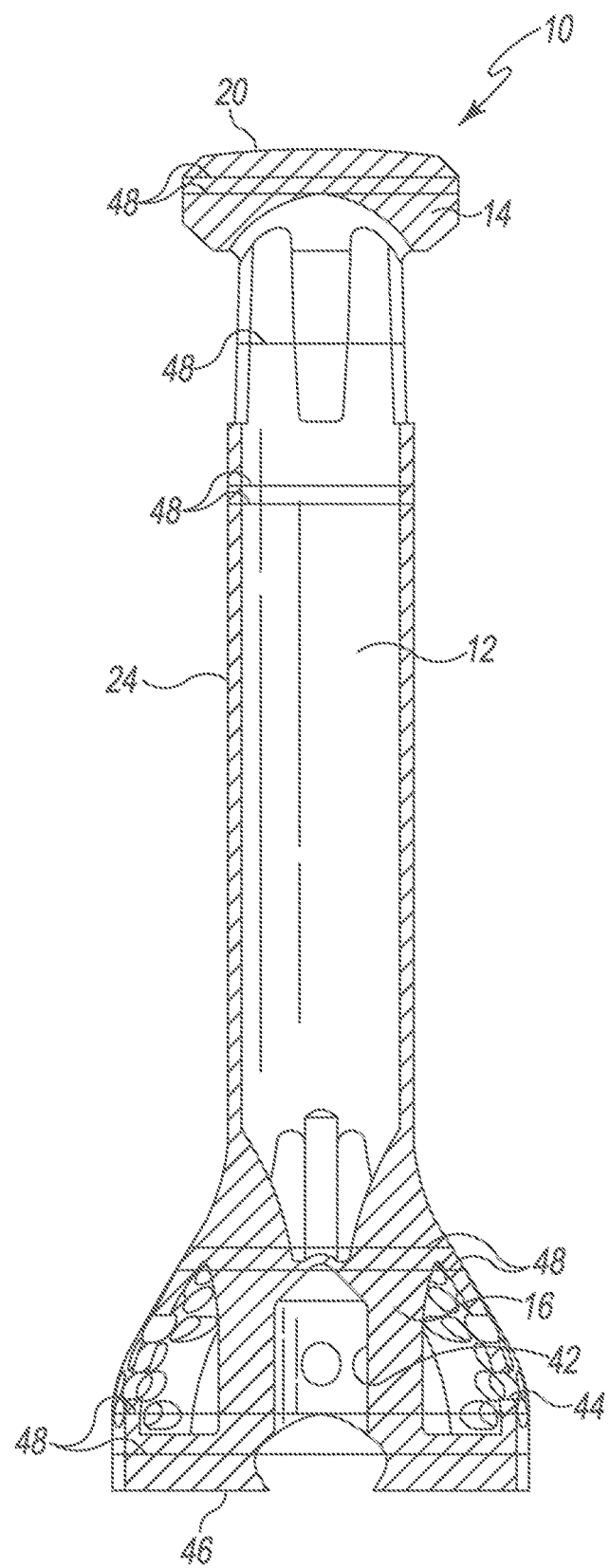
FIG. 6 is a cross sectional view of the impaction handle taken along the line 6-6 of FIG. 1, as viewed in the direction of the arrows, note the locking mechanism has been removed from the impaction handle in FIG. 6 for clarity of description.
Figure 7:
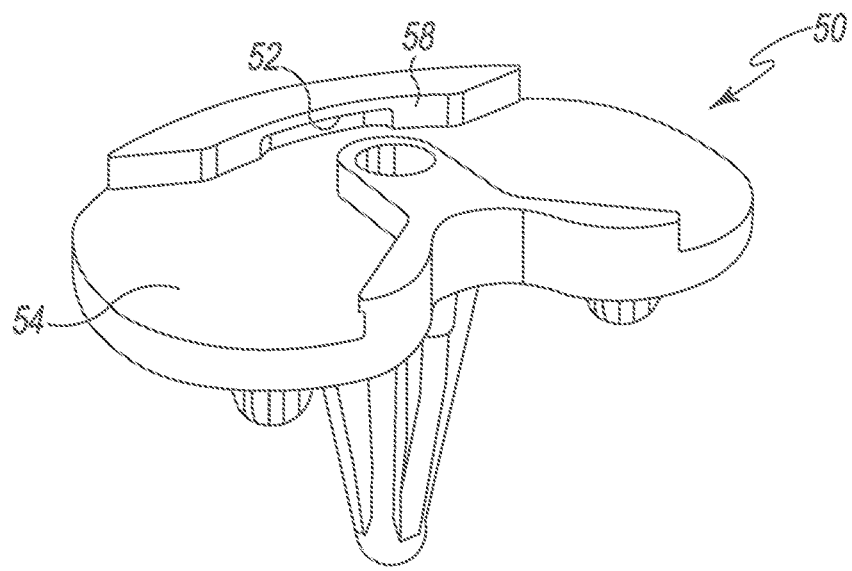
FIG. 7 is a perspective view of a tibial tray of an orthopaedic knee prosthesis.

As can be seen in FIG. 6, the impaction handle 10 has a substantially open internal structure. Such an open internal structure of the impaction handle 10 efficiently directs energy from an input force (i.e., the strike force applied by the surgeon) thereby resulting in greater efficiency of the output force (i.e., the force applied on the tibial tray 50 through the impact head 16). As can be seen in FIG. 6, to facilitate such an open internal structure design, the elongated shaft 12 is hollow along its entire length. Similarly, unlike conventional impactor designs, the impact head 16 of the impaction handle 10 is not a solid internal structure, but rather, similarly to the elongated shaft 12, is open in design. For example, as can be seen in FIG. 6, the impact head 16 includes an internal cavity 42 configured to house the slidable flange 26 and eccentric cylinder 32 of the locking mechanism 18. Moreover, the tapered sides of the impact head 16 are hollow and defined by a perforated skirt 44 as opposed to a solid structure. As can be seen in FIGS. 1, 2, and 6, the distal ends of the skirt 44 cooperates with the distal end of the central body of the impact head 16 to define an impact surface 46 that is sized and shaped to be positioned on a superior surface 54 of the tibial tray 50 when the impaction handle 10 is used to impact the tibial tray 50.

The open internal structure design of the impaction handle 10 significantly improves the impact load transfer efficiency (i.e., impact load transfer efficiency=output force/input force) of the handle relative to similarly externally-shaped handles of conventional design. In testing, specimens designed with the open internal structure design of the impaction handle 10 demonstrated an average impact load transfer efficiency of 66%. By comparison, similarly externally-shaped specimens of conventional design demonstrated an average impact load transfer efficiency of 30%. As a result, the open internal structure design of the impaction handle 10 allows for a greater transfer force onto the tibial tray 50 irrespective of strike velocity relative to similarly externally-shaped conventional handle designs. Similarly, less strike force is required for the open internal structure design of the impaction handle 10 to deliver a desired output force relative to similarly externally-shaped conventional handle designs.

Figure 9:
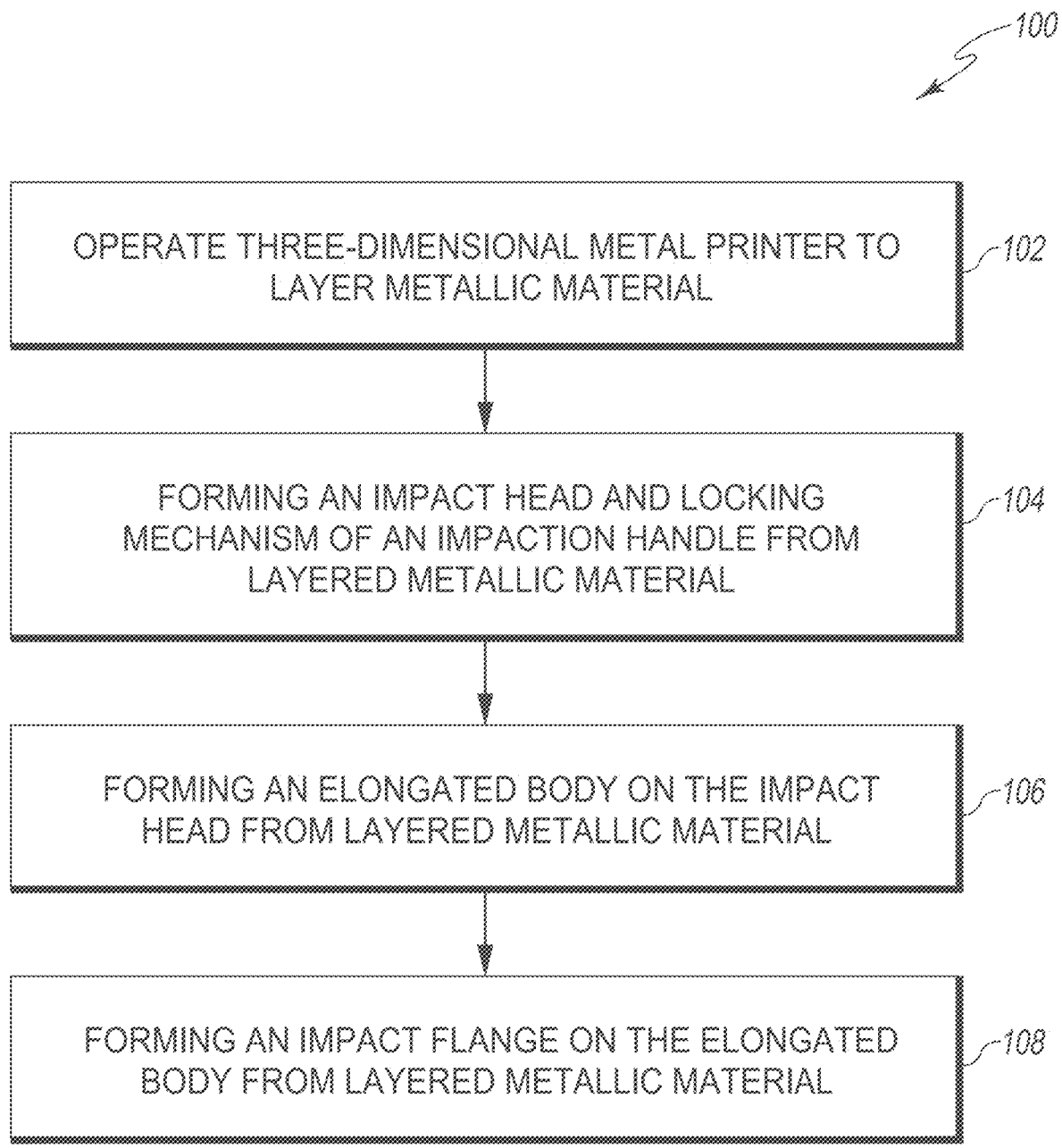
FIG. 9 is a flowchart illustrating a method of using a three-dimensional printer to form the impaction handle of FIG. 1.

In order to produce such an open internal structure design, the impaction handle 10 may be formed by DMLS, which, as described above, is a form of 3-D printing technology. In DMLS, the impaction handle 10 is formed in a layer-by-layer fashion using laser sintering in which light fuses metallic powder, forming the metallic structures that define the handle (i.e., the elongated shaft 12, the impact plate 14, the impact head 16, and the locking mechanism 18). As part of the process of fabricating the impaction handle 10, the metallic powder may be fused in layers, resulting in an orthopaedic surgical instrument that is a single monolithic component that includes a plurality of fused laminations 48. For example, as shown illustratively (not to scale) in FIGS. 4-6, the impaction handle 10 includes a plurality of fused laminations 48 of metallic material of uniform thickness that define the components of the handle (i.e., the elongated shaft 12, the impact plate 14, the impact head 16, and the locking mechanism 18). It should be appreciated that for clarity of description only a few illustrative laminations 48 are shown in FIGS. 4-6. In practice, given the nature of 3-D printing technology, the impaction handle 10 actually includes hundreds, if not thousands, of laminations 48. Moreover, in the perspective of FIGS. 4-6, the laminations 48 are shown as being generally horizontally disposed. However, it should be appreciated that the impaction handle 10 may be 3-D printed in any suitable orientation and thus any suitable orientation of the laminations 48. It should be further appreciated that other forms of 3-D printing technology such as, for example, optical fabrication, photo-solidification, or resin printing may be used to fabricate the impaction handle 10. For example, FIG. 9 is a flowchart showing a method 100 comprising the steps 102-108 implemented to form the different components of the impaction handle simultaneously. For example, FIG. 9 shows a method 100 that executes steps 102-108 to simultaneously form the different components of the impaction handle.

Figure 8:
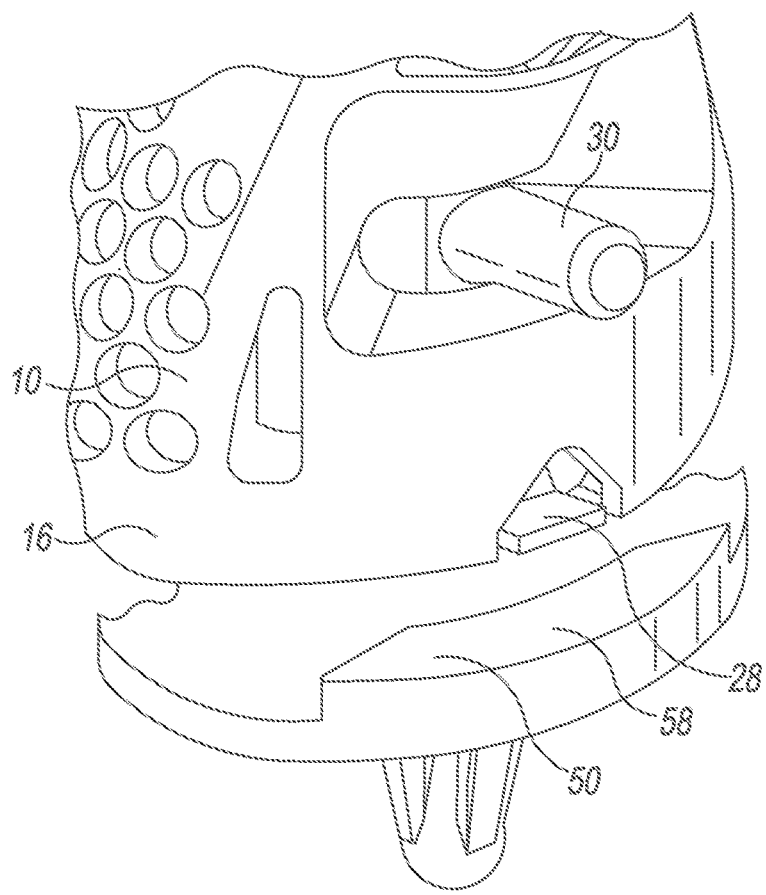
FIG. 8 is perspective view showing the impaction handle of FIG. 1 being secured to the tibial tray of FIG. 7.

In use, the impaction handle 10 may be utilized by a surgeon to implant the tibial tray 50 into the surgically-prepared proximal end of a patient's tibia. To do so, the surgeon first secures the tibial tray 50 to the tool 10. Specifically, as shown in FIG. 8, the impact head 16 of the impaction handle 10 is placed on the superior surface 54 of the tibial tray 50 such that the locking tab 28 of the handle's locking mechanism 18 is positioned proximate to the slot 52 formed in the anterior buttress 58 of the tray 50. Thereafter, the surgeon moves the lever 30 in a rightward direction (as viewed in the perspective of FIGS. 3 and 8) thereby extending the locking tab 28 outwardly from the impact head 16 and into the tray's slot 52 thus securing the tibial tray 50 to the impaction handle 10.

Thereafter, the surgeon uses the impaction handle 10 to position the tibial tray 50 such that its inferior bone-engaging surface, including its stem, is positioned relative to the patient's surgically-prepared proximal tibia in a desired orientation. Once the tibial tray 50 is positioned in such a manner, the surgeon strikes the impact plate 14 of the impaction handle 10 with a surgical mallet, sledge, or other impaction tool to drive the tibial tray 50 into the bone tissue until the tibial tray 50 is fully seated on the patient's surgically-prepared proximal tibia.

The surgeon then releases the tibial tray 50 from the impaction handle 10. To do so, the surgeon moves the lever 30 in a leftward direction (as viewed in the perspective of FIGS. 3 and 8) thereby retracting the locking tab 28 inwardly toward the impact head 16 and out of the tray's slot 52 thus releasing the impaction handle from the tibial tray 50.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

For example, it should be appreciated that the concepts described herein may be utilized in the design of impaction handles for use in implanting other types of orthopaedic implants such as hip implants, shoulder implants, or other components (e.g., femoral) of a knee prosthesis.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An orthopaedic surgical instrument for use during a surgical procedure to implant a tibial tray into a surgically-prepared proximal end of a tibia, comprising:
   an impaction handle, comprising:
      an impact plate defining a proximal end of the impaction handle, an impact head defining a distal end of the impaction handle, the impact head having an impact surface that is sized and shaped to be positioned on a superior surface of the tibial tray when the impaction handle is used to impact the tibial tray,
      an elongated shaft extending between the impact plate and the impact head, the elongated shaft being hollow along its entire length, and
      a locking mechanism positioned in the impact head, the locking mechanism comprising (a) a locking tab that is movable between (i) a locked position in which the locking tab is extended outwardly from the impact head so as to be received into a locking slot defined in the tibial tray, and (ii) an unlocked position in which the locking tab is retracted inwardly toward the impact head so as to remove the locking tab from the locking slot of the tibial tray, and (b) an eccentric cylinder having a tip, wherein (i) the locking tab is defined in an end of a flange, (ii) the flange is slidable relative to the impact head so as to move the locking tab between its locked position and its unlocked position, (iii) the tip of the eccentric cylinder is positioned in a slot defined in the flange, and (iv) rotation of the of the eccentric cylinder causes the flange to slide relative to the impact head,
   wherein the impact plate, the impact head, the elongated shaft, and the locking mechanism of the impaction handle collectively define a single monolithic metallic component.

2. The orthopaedic surgical instrument of claim 1, wherein the single monolithic metallic component defined by the impact plate, the impact head, the elongated shaft, and the locking mechanism of the impaction handle comprises a plurality of laminations.

3. The orthopaedic surgical instrument of claim 1, wherein:
   the single monolithic metallic component defined by the impact plate, the impact head, the elongated shaft, and the locking mechanism of the impaction handle comprises a plurality of laminations, and
   at least one of the plurality of laminations defines a portion of each of the impact head, the flange of the locking mechanism, and the eccentric cylinder of the locking mechanism.

4. The orthopaedic surgical instrument of claim 3, wherein at least one of the plurality of laminations defines a portion of each of the impact head, the flange of the locking mechanism, and the tip of the eccentric cylinder of the locking mechanism.

5. The orthopaedic surgical instrument of claim 1, wherein:
   the eccentric cylinder rotates about an axis of rotation, and
   the tip of the eccentric cylinder has a longitudinal axis that is offset from the axis of rotation of the eccentric cylinder.

6. The orthopaedic surgical instrument of claim 1, wherein:
   the eccentric cylinder has a lever extending outwardly therefrom, and
   movement of the lever causes rotation of the eccentric cylinder.

7. An orthopaedic surgical instrument for use during a surgical procedure to implant a tibial tray into a surgically-prepared proximal end of a tibia, comprising:
   a single monolithic metallic impaction handle including a plurality of laminations of metallic material, comprising:
      an impact plate defining a proximal end of the impaction handle,
      an impact head defining a distal end of the impaction handle, the impact head having an impact surface that is sized and shaped to be positioned on a superior surface of the tibial tray when the impaction handle is used to impact the tibial tray,
      an elongated shaft extending between the impact plate and the impact head, the elongated shaft being hollow along its entire length, and
      a locking mechanism positioned in the impact head, the locking mechanism comprising (a) a locking tab that is movable between (i) a locked positioned position in which the locking tab is extended outwardly from the impact head so as to be received into a locking slot defined in the tibial tray, and (ii) an unlocked position in which the locking tab is retracted inwardly toward the impact head so as to remove the locking tab from the locking slot of the tibial tray, and (b) an eccentric cylinder having a tip, wherein (i) the locking tab is defined in an end of a flange, (ii) the flange is slidable relative to the impact head so as to move the locking tab between its locked position and its unlocked position, (iii) the tip of the eccentric cylinder is positioned in a slot defined in the flange, and (iv) rotation of the of the eccentric cylinder causes the flange to slide relative to the impact head.

8. The orthopaedic surgical instrument of claim 7, wherein at least one of the plurality of laminations defines a portion of each of the impact head, the flange of the locking mechanism, and the eccentric cylinder of the locking mechanism.

9. The orthopaedic surgical instrument of claim 7, wherein at least one of the plurality of laminations defines a portion of each of the impact head, the flange of the locking mechanism, and the tip of the eccentric cylinder of the locking mechanism.

10. The orthopaedic surgical instrument of claim 7, wherein:
   the eccentric cylinder rotates about an axis of rotation, and
   the tip of the eccentric cylinder has a longitudinal axis that is offset from the axis of rotation of the eccentric cylinder.

11. The orthopaedic surgical instrument of claim 7, wherein:
   the eccentric cylinder has a lever extending outwardly therefrom, and
   movement of the lever causes rotation of the eccentric cylinder.

* * * * *